United States Patent
Larijani et al.

(10) Patent No.: US 7,528,172 B2
(45) Date of Patent: May 5, 2009

(54) COMPOSITIONS AND METHODS FOR IMPROVING RECOVERY AFTER GENERAL ANESTHESIA

(75) Inventors: Ghassem E. Larijani, Villanova, PA (US); Michael E. Goldberg, Philadelphia, PA (US)

(73) Assignee: The Cooper Health System, Inc., Camden, NJ (US)

( * ) Notice: Subject to any disclaimer, the term of this patent is extended or adjusted under 35 U.S.C. 154(b) by 671 days.

(21) Appl. No.: 10/677,678

(22) Filed: Oct. 2, 2003

(65) Prior Publication Data

US 2004/0143021 A1    Jul. 22, 2004

Related U.S. Application Data

(60) Provisional application No. 60/441,453, filed on Jan. 21, 2003, provisional application No. 60/501,432, filed on Sep. 9, 2003.

(51) Int. Cl.
*A61K 31/165*    (2006.01)

(52) U.S. Cl. ..................................... 514/618

(58) Field of Classification Search ................ 514/618
See application file for complete search history.

(56) References Cited

OTHER PUBLICATIONS

2002 Physician's Desk Reference, pp. 1193-1196.
Caldwell et al., "A double-blind, placebo-controlled investigation of the efficacy of modafinil for sustaining the alertness and performance of aviators: a helicopter simulator study", Psychopharmacology 2000 150:272-282.
Marshall et al., "Discharge Criteria and Complications After Ambulatory Surgery", Anesth Analg. 1999 88:508-517.
Myles et al., "Patient satisfaction after anaesthesia and surgery: results of a prospective survey of 10 811 patients", British Journal of Anaesthesia 2000 84(1):6-10.
Wu et al., "Systematic Review and Analysis of Postdischarge Symptoms after Outpatient Surgery", Anesthesiology 2002 96:994-1003.

*Primary Examiner*—Zohreh A Fay
(74) *Attorney, Agent, or Firm*—Michael B. Fein; Cozen O'Connor

(57) ABSTRACT

Compositions and methods for improving recovery following general anesthesia are provided. The composition comprises an effective dose of modafinil. Modafinil has been shown to reduce the symptoms associated with post-operative general anesthesia, improving the recovery form anesthesia.

1 Claim, No Drawings

ND METHODS FOR
IMPROVING RECOVERY AFTER GENERAL
ANESTHESIA

INTRODUCTION

This application claims the benefit of U.S. Provisional Application No. 60/441,453, filed Jan. 21, 2003 and U.S. Provisional Application No. 60/501,432 filed Sep. 9, 2003.

BACKGROUND OF THE INVENTION

With the goals of reducing health care costs and maximizing available health resources, there is an increasing trend towards providing surgical services through outpatient clinics, whenever possible. More than two thirds of patients receiving general anesthesia today are scheduled for same day discharge (Marshall, S. I. and F. Chung. 1999. *Anesth. Analg.* 88:508-517). Thus, there is significant emphasis placed on minimizing postoperative symptoms in order to facilitate early discharge. Basic criteria for discharge include stability of vital signs (including pain) within an acceptable range, ability to tolerate oral liquids, acceptable degree of nausea, and the ability to maintain an upright position without orthostasis (Marshall, S. I. and F. Chung. 1999. *Anesth. Analg.* 88:508-517). Further recovery is expected to take place at home after discharge. Recovery from anesthesia and surgery can be associated with residual sedation, pain, nausea, and vomiting (Marshall, S. I. and F. Chung. 1999. *Anesth. Analg.* 88:508-517; Myles, P. S. et al. 2000. *Br. J. Anesth.* 84:6-10).

Relatively few studies have evaluated recovery after discharge. Further, the available studies have deficiencies (i.e., partial reporting, non-uniformity of data collection techniques) that affect the utility of the study for drawing conclusions about recovery and postoperative symptoms following surgery with general anesthesia. The overall incidence of post-discharge symptoms in outpatients is reported to be approximately 45% for pain, 42% for drowsiness, 21% for fatigue, 18% for dizziness, 17% for nausea, and 8% for vomiting (Wu, C. L. et al. 2002. *Anesthesiology* 96:994-1003). Approximately 14% of patients undergoing general anesthesia experience these symptoms for 3 or more days (Myles, P. S. et al. 2000. *Br. J. Anesth.* 84:6-10), with 62% of patients requiring an average of 3.2 postoperative days to resume activities of daily living because of persistence of symptoms (Wu, C. L. et al. 2002. *Anesthesiology* 96:994-1003). Such statistics, however, do not describe the severity of symptoms.

Modafinil (PROVIGIL®, Cephalon Inc.) is a wakefulness-promoting agent approved by the FDA for patients with excessive daytime sleepiness associated with narcolepsy. The precise mechanism(s) through which modafinil promotes wakefulness is unknown. Modafinil is chemically un-related to typical central nervous system stimulants (i.e., amphetamines, methylphenidate), and has a pharmacological profile different than that of sympathomimetic amines. During clinical trials, modafinil (200 mg/d and 400 mg/d) was shown to significantly improve daytime wakefulness without affecting nighttime sleep (reviewed in 2002 *Physician's Desk Reference*, pages 1193-1196). In addition, modafinil has been shown to reduce fatigue and confusion in sleep-deprived pilots (Caldwell, J. A. et al. 2000. *Psychopharmacology* 150: 272-282). Some of modafinil's pharmacological effects appear to be the type of effects that would counter the symptoms experienced by patients recovering from general anesthesia (i.e., feeling tired, sleepy and dizzy).

It has now been found that modafinil administration to patients decreases the severity of postoperative symptoms commonly associated with general anesthesia thus improving recovery from general anesthesia.

SUMMARY OF THE INVENTION

The present invention provides compositions and methods for improving recovery from general anesthesia using modafinil. Modafinil is administered in a pharmaceutically acceptable formulation to reduce the symptoms associated with recovery.

DETAILED DESCRIPTION OF THE INVENTION

The present invention is a composition for improving postoperative recovery by decreasing symptoms associated with use of general anesthesia. The composition comprises modafinil, a drug currently approved by the U.S. Food and Drug Administration for treatment of narcolepsy. Clinical data has been collected which shows that modafinil was capable of decreasing post-operative symptoms in patients who underwent general anesthesia, thus decreasing the time to recovery of lifestyle following anesthesia. Therefore, the present invention is also a method of improving recovery in patients undergoing general anesthesia comprising administering to a patient who has undergone general anesthesia a therapeutically effective oral dose of modafinil. In the context of the present invention, a "therapeutically effective dose" is a dose that has been shown to have a significant pharmacological effect, in this case the effect of reducing postoperative symptoms in patients undergoing general anesthesia. The symptoms monitored and shown to be affected by modafinil treatment included fatigue and exhaustion, level of energy, mental alertness, and ability to concentrate. All of the symptoms monitored after treatment with modafinil and shown to be affected by use of the drug are ones that led to an improvement in the overall recovery of the patients following surgery.

Informed consents were obtained from patients scheduled to undergo outpatient surgical procedures under general anesthesia to participate in this prospective study approved by an institutional review board. In this study, the clinical activity of modafinil to improve recovery post-anesthesia was examined in a randomized, double blind, parallel group study. Thirty-four (34) patients scheduled for same day surgery under general anesthesia participated in this prospective study. Patients were American Society of Anesthesiology physical status I-II, with a Body-Mass-Index<40 without any known significant renal, hepatic, cardiovascular, neurological, gastrointestinal, endocrine, hematologic, or pulmonary diseases as judged by the investigator. A history of epilepsy, alcoholism, or chronic use of opioids also excluded the patients from participation in this study. Patients were asked to rate various symptoms they had experienced over the previous 24-hour period using a verbal analog scale (VAS) rating of 0 to 10, as well as discrete scores when indicated. The symptom evaluation included headache, dizziness, level of energy, appetite, nausea, pain, vomiting, degree of being tense, clear-headedness, restlessness, fatigue, exhaustion, quality of sleep during the previous night, need for the help from a caregiver, the ability to read, comprehend, and communicate.

Anesthetic management of the patients was at the discretion of the attending anesthesiologist. Patients were monitored post-operatively, and cared for according to institutional standards. Once the patient was able to tolerate oral intake of liquids, the study drug (modafinil, 200 mg) or placebo was administered, randomly, with a sip of water. Patients were discharged according to institutional standards. Patients were contacted 24 (±1) hours after dosing for symptom evaluation and the same questions were asked. Patients were also asked whether the study drug they received had any beneficial effect. If the patient felt they received a benefit from the study drug they were asked to describe the benefit in their own words.

The study group included 24 female and 10 male patients (n=17 per group). The demographics of the groups are shown below in Table 1. There were no significant differences in age, height, weight, or gender distribution between the two groups.

TABLE 1

Demographic Data

| Variable | Modafinil | Placebo |
|---|---|---|
| Age (years) | 42 ± 10 | 41 ± 12 |
| Weight (pounds) | 176 ± 33 | 178 ± 39 |
| Height (inches) | 65 ± 3.2 | 67 ± 3.4 |
| Gender | 4 males, 13 females | 6 males, 11 females |

Almost all patients had received the same type of anesthetic management including propofol, a narcotic, a volatile agent, a muscle relaxant, nitrous oxide, and oxygen. Patients had undergone mostly orthopedic or gynecological surgical procedures. Surgical procedures or the exact doses of anesthetics were not compared between the groups.

There were no significant differences in preoperative symptoms reported between the two groups (modafinil versus placebo; Table 2). As expected, patients were tenser, more restless, and less relaxed pre-operatively (in both groups). Patients receiving modafinil had significantly less fatigue, were significantly less worn out, and were significantly less exhausted postoperatively than those receiving placebo. Significantly more patients in the placebo group complained of moderate-to-severe fatigue, feeling worn out, or being exhausted. Operative distress was defined as a lack of energy, presence of feeling worn out, fatigue, exhaustion, mental clouding, and problem reading (comprehending) (total of 60 possible points to define the most severe Operative distress). In the modafinil group, the point value for operative distress was 10.5±6.0, preoperatively, increasing to 11.3±9.1, postoperatively. The corresponding values for operative distress in the placebo group were 13.4±11.9, pre-operatively, and 21.0±13.8, post-operatively. Patients receiving modafinil had significantly less post-operative distress than those receiving placebo.

TABLE 2

Mean (± Standard Deviation) of the Verbal Analog Score for Symptoms Experienced in Modafinil (n = 17) and Placebo (n = 17) Groups

| Complaint | Status | Modafinil | Placebo |
|---|---|---|---|
| Energy | pre-operative | 7.5 (2.8) | 6.8 (2.8) |
| | post-operative | 6.2 (3.5) | 5.2 (2.7) |
| | difference | −1.3 | −1.6 |
| Appetite | pre-operative | 7.9 (2.9) | 6.4 (3.4) |
| | post-operative | 6.1 (3.8) | 6.8 (3.2) |
| | difference | −1.8 | 0.4 |
| Nausea | pre-operative | 0.6 (2.4) | 1.0 (1.7) |
| | post-operative | 1.9 (3.5) | 2.2 (3.3) |
| | difference | 1.3 | 1.2 |
| Restless | pre-operative | 4.5 (3.7) | 3.4 (3.6) |

TABLE 2-continued

Mean (± Standard Deviation) of the Verbal Analog Score for Symptoms Experienced in Modafinil (n = 17) and Placebo (n = 17) Groups

| Complaint | Status | Modafinil | Placebo |
|---|---|---|---|
| | post-operative | 2.5 (3.0) | 3.4 (3.1) |
| | difference | −2.0 | 0.0 |
| Tense | pre-operative | 5.4 (3.6) | 4.0 (3.2) |
| | post-operative | 2.2 (3.2) | 1.1 (2.1) |
| | difference | −3.2 | −2.9 |
| Worn out | pre-operative | 3.5 (3.4) | 2.5 (2.9) |
| | post-operative | 2.9 (2.4) | 4.7 (3.6)** |
| | difference | −0.6 | 2.2 |
| | % with rating ≥ 5 | 29% | 65%* |
| | % with rating > 3 | 41% | 65% |
| Fatigue | pre-operative | 1.6 (2.7) | 2.8 (3.0) |
| | post-operative | 1.4 (1.8) | 4.8 (3.3)* |
| | difference | −0.2 | 2.0 |
| | % with rating ≥ 5 | 12% | 65%* |
| | % with rating > 3 | 18% | 71%* |
| Exhaustion | pre-operative | 2.2 (3.3) | 2.3 (3.0) |
| | post-operative | 2.4 (3.1) | 4.3 (3.3)** |
| | difference | 0.2 | 2.0 |
| Ease of sleep | pre-operative | 6.5 (3.3) | 6.4 (3.3) |
| | post-operative | 6.2 (3.6) | 6.6 (0.9) |
| | difference | −0.3 | 0.2 |
| Reading ability | pre-operative | 9.0 (2.1) | 8.6 (1.9) |
| | post-operative | 9.2 (1.6) | 7.5 (3.6) |
| | difference | 0.2 | −1.1 |
| Mental limitation to resume activity | post-operative | 0.6 (1.6) | 1.5 (2.2) |

*p < 0.05 between the two groups
**p < 0.01 between the two groups

In addition to responding to questions related to assessment of post-operative symptoms, patients were asked to describe if the study drug, modafinil, benefited them. Content analysis of the comments made by the patients receiving modafinil revealed two major themes of "alertness" and "energy" expressed by 71% of the patients. Being "alert" was indicated by almost half of these patients. Typical statements were as follows: "Felt real alert", "not groggy", "more alert than the last time". Being "energetic" was indicated by another half. Typical statements are as follow: "did not feel tired", "more energy than past surgery". Such statements regarding energy level or alertness were expressed by only 18% of patients in the placebo group. The difference in proportions is both clinically and statistically significant (p<0.05). Four patients in the placebo group and one patient in the modafinil group complained of not being able to fall asleep at night; these patients had naps of a few hours after going home.

Recovery from anesthesia is a time dependent process. Depending on the definition, recovery from anesthesia may last days in a given patient. Most emphasis on recovery from anesthesia during the past 2 decades has been placed on facilitating patient discharge to reduce costs (Marshall, S. I. and F. Chung. 1999. *Anesth. Analg.* 88:508-517). Many clinicians expect further recovery to occur after discharge. Current discharge criteria include stability of vital signs within an acceptable range, no excessive pain requiring parenteral therapy, toleration of oral liquid, minimal nausea and vomiting, ability to stand up without orthostasis, and the presence of a responsible adult to escort the patient home (Myles, P. S. et al. 2000. *Br. J. Anesth.* 84:6-10). The emphasis on recovery from anesthesia has been concentrated on the ability to release a patient to their home, not on the presence of post discharge symptoms. The results of the current clinical study provide for an assessment of the effect of modafinil treatment on improving the recovery form anesthesia. In this study significantly more patients complained of moderate-to-severe fatigue in the placebo group (65% vs. 12%) as compared to the modafinil treatment group. Patients receiving placebo were sleepier and admitted to more episodes of napping after discharge to home; these patients also had more difficulty remaining asleep during the first night after discharge.

Therefore, these data showed that modafinil significantly reduced the degree of fatigue, degree of feeling worn out, feeling of exhaustion, The incidence of moderate-to-severe fatigue, and post-operative distress (defined above) associated with general anesthesia, resulting in an improved recovery from general anesthesia. In addition, modafinil significantly improved feelings of alertness, and energy in patients recovering from general anesthesia.

The present invention is a composition for improving recovery from general anesthesia in patients having undergone general anesthesia comprising modafinil in a pharmaceutically acceptable formulation. The present invention is also a method for improving recovery from general anesthesia in patients having undergone general anesthesia comprising administering to general anesthesia to a patient, monitoring the patient to determine that the patient is capable of ingesting liquids, and then administering a therapeutically effective dose of modafinil to the patient so that the symptoms associated with recovery from general anesthesia are reduced. Multiple dosing with the composition of the instant invention may be needed in those patients who experience an exaggerated depressive response to anesthetics. One of skill would understand how to choose an effective dose for administration to a patient as well as how to determine if multiple doses are needed.

What is claimed is:

1. A method for improving recovery from general anesthesia in patients having undergone general anesthesia comprising:
    a) administering general anesthesia to a patient;
    b) monitoring the patient to determine that the patient is capable of ingesting liquids; and
    c) administering a dose of modafinil to the patient so that the symptoms caused by the general anesthesia, said symptoms being selected from the group consisting of mental cloudiness, loss of reading comprehension, loss of mental alertness and inability to concentrate, are reduced is effective to increase the reading comprehension, loss of mental alertness, and inability to concentrate, are reduced.

* * * * *

UNITED STATES PATENT AND TRADEMARK OFFICE
CERTIFICATE OF CORRECTION

PATENT NO. : 7,528,172 B2  
APPLICATION NO. : 10/677678  
DATED : May 5, 2009  
INVENTOR(S) : Ghassem E. Larijani and Michael E. Goldberg Page 1 of 1

It is certified that error appears in the above-identified patent and that said Letters Patent is hereby corrected as shown below:

Col. 6, claim line 10
1. A method for improving recovery from general anesthesia in patients having undergone general anesthesia comprising:
a) administering general anesthesia to a patient;
b) monitoring the patient to determine that the patient is capable of ingesting liquids; and
c) administering a dose of modafinil to the patient so that the symptoms caused by the general anesthesia, said symptoms being selected from the group consisting of mental cloudiness, loss of reading comprehension, loss of mental alertness and inability to concentrate, are reduced.

Signed and Sealed this

Sixteenth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO.         : 7,528,172 B2                                    Page 1 of 1
APPLICATION NO.    : 10/677678
DATED              : May 5, 2009
INVENTOR(S)        : Ghassem E. Larijani and Michael E. Goldberg It is certified that error appears in the above-identified patent and that said Letters Patent is hereby corrected as shown below:

Col. 6, lines 10-23, claim 1 should read:
1. A method for improving recovery from general anesthesia in patients having undergone general anesthesia comprising:
a) administering general anesthesia to a patient;
b) monitoring the patient to determine that the patient is capable of ingesting liquids; and
c) administering a dose of modafinil to the patient so that the symptoms caused by the general anesthesia, said symptoms being selected from the group consisting of mental cloudiness, loss of reading comprehension, loss of mental alertness and inability to concentrate, are reduced.

This certificate supersedes the Certificate of Correction issued June 16, 2009.

Signed and Sealed this

Fourteenth Day of July, 2009

JOHN DOLL
*Acting Director of the United States Patent and Trademark Office*